United States Patent [19]
Paschalis et al.

[11] 3,938,953
[45] Feb. 17, 1976

[54] PROCESS AND DEVICE FOR BLOOD EXAMINATION USING SUBSTANCES LABELLED WITH RADIOACTIVE NUCLIDES

[75] Inventors: Stratos Paschalis, Frankfurt am Main; Rudolf Kern, Mainz; Karl-Friedrich Mück, Wiesbaden, all of Germany

[73] Assignee: Hoechst Aktiengesellschaft, Frankfurt am Main, Germany

[22] Filed: May 28, 1974

[21] Appl. No.: 474,056

[30] Foreign Application Priority Data
May 30, 1973 Germany............................ 2327576

[52] U.S. Cl.................. 23/230 B; 23/259; 23/292; 424/1
[51] Int. Cl.² ........................................ G01N 33/16
[58] Field of Search ............ 23/230 B, 253 TP, 259, 23/253 R, 292; 424/1

[56] References Cited
UNITED STATES PATENTS

| | | | |
|---|---|---|---|
| 3,376,114 | 4/1968 | Eberle | 23/230 B |
| 3,507,618 | 4/1970 | Murty et al. | 23/230 B |
| 3,646,346 | 2/1972 | Catt | 23/230 B |
| 3,743,482 | 7/1973 | Eisentraut | 23/230 B |
| 3,768,979 | 10/1973 | Mead et al. | 23/230 B |
| 3,826,619 | 7/1974 | Bratu, Jr. et al. | 23/230 B |

*Primary Examiner*—R. E. Serwin
*Attorney, Agent, or Firm*—Curtis, Morris & Safford

[57] ABSTRACT

A process and device for determining a hormone in a liquid such as blood wherein measured amounts of the liquid to be tested, of a radioactively-labelled hormone, and of a hormone-binding protein or antibody, all present in a measuring vial, are contacted with an adsorbing vial formed from a mixture of a thermoplastic resin and an ion exchange resin for adsorbing unbound hormone, and the residual radioactivity of the liquid mixture is then measured after draining back into said measuring vial.

11 Claims, 1 Drawing Figure

U.S. Patent  Feb. 17, 1976  3,938,953
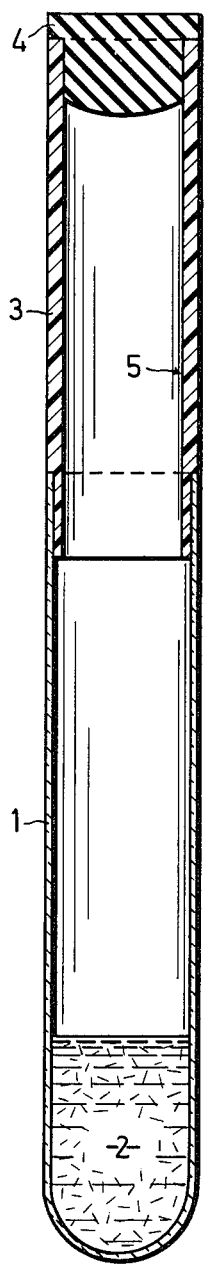

PROCESS AND DEVICE FOR BLOOD EXAMINATION USING SUBSTANCES LABELLED WITH RADIOACTIVE NUCLIDES

The present invention relates to a process and a device for the blood examination using substances labelled with radioactive nuclides.

More particularly this invention relates to a process and a device for the determination of hormones in liquids using compounds labelled with radioactive nuclides.

The hormones, synthesized in certain glands of the body and delivered to the circulating blood, are present in very low concentration. Only the use of indicators labelled with radioactivity has permitted their exact quantitative determination.

Accordingly to the chemical nature of the hormone under consideration two different methods for analysis are used. When having immunogenic properties, that is to say, when being able to produce suitable antibodies, the hormone is determined by the Radioimmunoassay (RIA). When devoid of immunogenic properties, it is determined by the competitive protein binding analysis. The two methods have in common that a certain amount of the hormone must be eliminated from the reaction solution by means of an ion exchanger or another substance suitable for this purpose.

According to known radio-immunochemical determination methods, for example a mixture of a known amount of a hormone unlabelled and the same one labelled with radioactivity is reacted with a specific antibody building a complex. The hormone is labelled with a suitable nuclide, such as, for example $^{125}I$, $^{131}I$, $^{14}C$, $^{3}H$. Between the antibody and the hormone a reaction equilibrium is brought about, slight amounts of the hormone being unbound. With constant antibody concentration this free part is directly proportional to the total amount of the hormone added. It is eliminated by means of a suitable adsorption agent and determined. A standard curve is drawn up permitting the determination of an unknown amount of the hormone.

In the competitive protein binding analysis which is also known, advantage is taken of the fact that hormones, especially those having a very low molecular weight, are bound and transported in the blood by specific proteins, for example, in the case of the two thyroid hormones Thyroxine and Triiodothyronine, by an $\alpha$-globuline, the "Thyroxine-Binding-Globuline" (TBG). These proteins can be used as primary complex forming agents for the hormone concerned, similar to the antibodies in the radioimmunochemical methods. The free hormone is separated from the solution and determined.

Another embodiment of this process is the determination of the capacity of the binding proteins in the serum. A slight amount of the radioactively labelled hormone is added to the serum in which the capacity of the binding protein for the same hormone is to be evaluated. Between the binding protein and the labelled hormone a reaction takes place in which the labelled hormone partially replaces the bound inactive one and partially reacts directly with the binding protein. The unbound moiety is eliminated from the solution by adsorption and is determined. This free part is inversely proportional to the free capacity of the serum protein under consideration.

In all these methods, the common step is the elimination of the free moiety of the hormone from the solution and its determination. Hitherto, ion exchangers, such as Amberlite $^{(R)}$ (registered trade mark) in the form of grains or embedded into polyurethane sponges or as strip, have been used for this purpose.

After the incubation of the solution with the adsorbing agent all these methods require additional time-consuming steps implying sources of error. Thus, when using ion exchange grains centrifuging is necessary after incubation in order to permit an unobjectionable pipetting of the supernatent. Sometimes, the grains are additionally washed several times before the measurement. It is true that the use of strips and sponges is an advance upon the grains but it is complicated and time-consuming, because the strip must be kept moist before its use and its eilimination from the solution can lead to erroneous results (drops on the strip). When using the ion exchanger sponge, care must be taken that the air is eliminated from the sponge before the adsorption procedure and the sponge is thoroughly washed after the incubation.

The present invention provides a process for determining the concentration of hormones in liquids by adding the hormone to be determined in radioactively labelled form as indicator, as well as antibodies or hormone binding proteins which react with the hormone to be determined, following adsorption separation of the unbound indicator and determination of the residual radioactivity of the liquid, which process comprises introducing determined amounts each of a solution of the radioactively labelled hormone and the antibody or the hormone binding protein and a determined amount of the liquid to be examined into a measuring vial, connecting the latter with an adsorption vial the inner surface of which has adsorptive properties with regard to the hormone to be determined, closing this device, bringing the liquid therein into contact with the inner surface of the adsorption vial over a certain period of time and measuring thereafter the residual activity of that liquid in usual manner after it has flowed down into the measuring vial.

It is a preferred embodiment of the process of the invention to stack or screw the adsorption vial onto the measuring vial so that the liquid is brought into contact with the inner surface of the adsorption vial several times and to turn the device consisting of the measuring vial and the adsorption vial round an axis in 90° position to the cylinder axis. It is also possible to shake the device.

The process is carried out by introducing into the measuring vial the liquid to be examined which contains the hormone and the binding protein or the antibody and, optionally, additional solutions of substances as well as the radioactively labelled hormone, putting on the adsorption vial, closing the device and measuring the radioactivity of the liquid in the measuring vial. The device (measuring and adsorption vial) is fixed on a rotator and turned for a definite period of time round an axis in 90° position to the cylinder axis. During this process the solution comes into contact with the inner surface of the adsorption vial several times, the free moiety of the hormone being adsorbed and thus eliminated from the solution. After the adsorption is completed, the device is put upright to allow the liquid to flow from the adsorption vial down to the measuring vial and to leave back the hormone moiety adsorbed at the surface. In doing so, the two moieties are separated.

The activity still remaining in the solution is now measured, for example in a well type scintillation counter or in an automatic gamma sample changer, without taking off the adsorption vial. The fact that the adsorption vial need not be taken off is a great advantage because contaminations thus are avoided. Pipetting is not necessary, either.

The process of the invention advantageously allows determining the concentration of a hormone in the blood. The TBG capacity is determined, for example, by introducing into a measuring vial a sufficient amount of radioactively labelled L-triiodothyronine ($T_3^*$) dissolved in a suitable buffer and adding the serum to be examined. The specific activity of the $T_3^*$ used can range between 10–200 mCi/mg $T_3$ which values may also be lower or higher, in principle. As buffer solution any system can be used which has a sufficient buffer capacity at pH 5–9, for example, tris(-hydroxymethyl)-amino-methane/HCl or phosphate according to Sorensen. Advantageously, the pH of the buffer solution ought to be 7, but it may also be higher or lower. The $T_3^*$ reacts with the TBG whereby it is bound by it for the greatest part. Now, the adsorption vial is stacked on, the whole device is closed and the initial radioactivity is measured, for example, in a well type scintillation counter or an automatic gamma sample exchanger. The length of the adsorption vial stacked on can, advantageously, vary between 1 and 6 cm, depending on the number of the adsorption places per surface unit. The device according to the invention is fixed on a rotator, for example, allowing it to rotate over a determined period of time, the liquid being brought into contact several times with the inner surface of the adsorption vial. During this process, the $T_3$ — labelled and not labelled — is adsorbed in the adsorption vial and so eliminated from the solution. After the adsorption is completed, the device is put upright and the activity which has remained in the solution is measured after several minutes, as has been described.

The process of the invention can be used in corresponding manner for the absolute determination of the thyroid gland hormones Thyroxine and Triiodothyronine. For this purpose, a TBG solution of constant capacity is necessary by means of which a standard curve is drawn up. The TBG solution can be prepared according to known processes of column chromatography. To that solution, radioactively labelled Thyroxine ($T_4^*$) is added which is bound according to the equation $T_4 + TBG \rightleftarrows TBG \cdot T_4^*$. When unlabelled Thyroxine ($T_4$) is added to that solution, a part of the labelled Thyroxine bound to the TBG is expelled and is under free form. As this amount of the expelled labelled thyroxine is directly proportional to the unlabelled thyroxine added, a relation between the free $T_4^*$ and the $T_4$ added is established which can be illustrated diagrammatically in the form of a standard curve.

The $T_4$ content in the serum is determined by setting free the thyroid gland hormones by denaturating the binding proteins with alcohol. The alcoholic extract of L-Triiodothyronine ($T_3$) and Thyroxine ($T_4$) can be evaporated to a concentrate which can be redissolved. An aliquot part of the solution is added to the TBG-$T_4^*$ solution in the measuring vial by pipetting, the adsorption vial is put on in accordance with the invention and turned, for example, for 1 hour similar to the $T_3$ determination. In this process the free $T_4^*$ is adsorbed in the adsorption vial and thus eliminated from the solution. The amount of $T_4$ of the serum to be examined can be evaluated from the quotient residual radioactive/initial radioactivity by means of the standard curve. The value read off is indicated to be $T_4$ because the amount of $T_3$ is very small in comparison thereto.

The process of the invention can be used in corresponding manner to determine the hormones by radioimmunochemical methods (Radioimmunoassay).

The present invention also provides a device for performing the process according to the invention which device consists of two vials detachably connected with each other the measuring vial of which, closed at the bottom, contains the liquid to be examined, a solution of the radioactively labelled hormone and the antibody or the hormone binding protein and the adsorption vial of which, capable of being closed at the extremity, is provided with an inner layer having adsorptive properties with respect to the hormone to be determined.

The device of this invention is illustrated diagrammatically by way of example in the accompanying drawing in which is referred as follows: measuring vial 1, liquid, solution of the radioactively labelled hormone and the antibody or the hormone binding protein to be examined 2, adsorption vial 3, closure 4, adsorptive layer 5.

The measuring vial can be made of glass or of plastic materials, preferably of polyethylene. Its length and breadth may vary and depend on the volumes available of the liquids to be examined or the diameter of the well type scintillation counter.

The adsorption vial consists of a thermoplast which contains 10–60 percent by weight of an ion exchanger. High-pressure polyethylene is preferred which contains 20–40 percent by weight of an anion exchanger carrying quaternary amino groups capable of being ionized. The length of the adsorption vials depends on the exchanger activity and is advantageously 1 to 6 cm.

The adsorption vial is advantageously manufactured by thermoplastic transformation of homogenised mixtures of thermoplasts and suitable ion exchangers. Suitable thermoplasts are the polymers which are transformed at a temperature ranging from 100°C to 200°C, preferably from 130°C to 170°C. There may be used, for example:

Polyethylene: high-pressure polyethylene having melt indices ($i5$) of from 0.3 to 70, preferably from 0.3 to 10, measured according to German standard DIN 53735 at 190°C: low-pressure polyethylene having melt indices ($i5$) of from 0.3 to 30, preferably from 10 to 30, measured according to German standard DIN 53735 at 190°C.

Polypropylene having melt indices ($i2$) of from 0.4 to 40, preferably from 5–30, measured according to German standard DIN 53735 E at 230°C.

Polyoxymethylene: obtained by homo or copolymerization of trioxane and formaldehyde and cyclic acetals having melt indices ($i2$) of from 1 to 50, preferably from 15 to 50 measured according to German standard DIN 53735 at 190°C.

Polystyrenes having melt indices ($i5$) from 2 to 30, preferably from 5 to 25, measured according to DIN 53735 at 200°C.

Poly(meth)acrylates having melt indices of from 0.4 to 10, preferably from 5 to 10, measured according to ASTMD 1238-62 T.

Polyvinyl chloride having K-values of from 40–80, preferably from 50–70, measured according to DIN 53726 in cyclohexanone at 25°C.

Polyester from dibasic carboxylic acids and diols, among which polyester from linear aliphatic dicarboxylic acids having 4 to 12 carbon atoms and $\alpha,\omega$-diols having from 2 to 8 carbon atoms, for example, sebacid acid/ethylene glycol polyesters are especially suitable.

Polyamides from dibasic dicarboxylic acids and diamines, the melting point of the polymers being reduced by the introduction of, for example, ether, methylol or ester groups or by cocondensation.

As ion exchangers, there may be admixed anion and cation exchangers having medium particle sizes from 0.04 to 1.0 mm diameter, preferably from 0.08 to 0.2 mm diameter. The exchange capacity is 0.3 to 3 Val/l, preferably 0.5 to 1.5 Val/l. Generally, the exchange resins are cross-linked, the cross-linking portion ranging from 1 to 12 percent, preferably from 4 to 10 percent. Suitable ion exchangers in powder form available in commerce are Amberlite (R) CG 400, Amberlite (R) IRA 402, Amberlite (R) 200 and Dowex (R) (registered trade marks).

The mixtures of thermoplasts and ion exchanger, which advantageously contain from 10 to 60 percent by weight, preferably from 20 to 40 percent by weight of exchange resin, are homogenized on rollers, calanders, kneaders or extruders, preferably double screw extruders, at a temperature ranging from 100°C to 200°C, preferably from 130°C to 170°C.

The adsorption vials can be manufactured on extruders or on injection molding machines.

In the extrusion procedure, the homogenized mixture is preferably carried through a tubular die at a temperature ranging from 130°C to 170°C and synchronously taken off over a gaging tank under a negative gage pressure of from 1 to 15 m water column, preferably from 2 to 10 m water column. The endless tube thus obtained is cut to the length corresponding to that of the adsorption vials and the outer surface is turned off at the extremities to guarantee a tight closure between the adsorption vial and the measuring vial and the cap.

In the injection molding, the mixture is worked within the same temperature range. The tube thus obtained has the dimensions necessary for the tightness of the device of the invention. Afterwards, the inner surface of the shaped article can be bored open in this case in order to improve the adsorptive properties.

The process and device of the invention allow a simpler and safer determination of the hormones, especially with respect to the separation of the feee moiety of the hormone from the solution. Complicated steps, such as pipetting, centrifuging and washing are no longer necessary. The values obtained are very well reproducible.

Surprisingly, it was found that the adsorption vial of thermoplastic material and ion exchanger did not show any swelling processes which could make burst the measuring vial being tightly connected.

EXAMPLES OF MANUFACTURE (ADSORPTION VIAL)

EXAMPLE 1

Low pressure polyethylene having 30 % of Amberlite (R) CG 400 I (registered trade mark), chloride form, was dried over night under reduced pressure and granulated on a double screw extruder after mixing through. The granules were dried, and an extruder was used to produce an endless tube. From the tube produced according to that process pipes 6 cm long were cut and used for adsorption.

EXAMPLE 2

High pressure polyethylene having 35 % Amberlite (R) CG 400 (registered trade mark) in chloride form were dried for 24 hours under reduced pressure, thoroughly mixed and granulated on a double screw extruder. The dried granules were used for the production of an endless tube from which pipes 5 cm long were cut and used for adsorption.

EXAMPLE 3

Granules of high pressure polyethylene having 35 % Amberlite CG 400 I (registered trade mark) in chloride form were used for the production of injection-molded pipes 5 cm long.

EXAMPLE OF APPLICATION: DETERMINATION OF THE TBG CAPACITY a. Preparation of the L-triiodothyronine-$I^{125}$ solution.

A corresponding amount of L-triiodothyronine-$I^{125}$ ($T_3$\*) having the specific activity 100 mCi/mg $T_3$ was added to a solution of 1 % tris(hydroxymethyl)-aminomethane the pH of which was adjusted to 7.4 with conc.hydrochloric acid, so that the concentration of radioactivity was about 0.7 $\mu$Ci/ml.

b. Standard serum

Serum having normal TBG binding capacity obtained from the blood of human beings having a thyroid gland with normal function.

c. Determination of the TBG capacity.

About 5 ml of blood were taken from the patient the thyroid gland function of whom was to be examined. From the serum obtained therefrom after coagulation and centrifuging of the blood corpuscles 0.2 ml were pipetted into a measuring vial made of polypropylene which contained 3.3 ml of the $T_3$\* solution, the adsorption vial manufactured according to examples 1 to 3 was put thereon, the device was closed and the whole was allowed to stand for about 10 minutes. The corresponding procedure was applied to the standard serum. During that period of time the total radioactivity of the liquid was measured in a well type scintillation counter or in an automatic gamma sample changer. Thereafter, the device was fixed on a rotator and turned for an hour with 13 revolutions per minute. The device was set up, the liquid in the adsorption vial was allowed to flow downwards and the activity remaining in the liquid phase was measured. The measurement was performed by calculating the quotient G = residual activity : initial activity as to the patient and the standard serum and the thyroxine binding capacity in percentages of the patient serum according to the equation $$TBK\ [\%] = \frac{G(\text{patient serum})}{G(\text{standard serum})} \cdot 100$$

Generally, the TBK value rises as compared to the normal serum in the presence of a hypothyreosis and falls in the presence of a hyperthyreosis.

EXAMPLE 5

Determination of the thyroxine concentration in the serum 0.5 ml each of the serum to be examined and the control serum with a known amount of not labelled $T_4$ were introduced each time in a vial capable of being centrifuged of each 1.0 ml and mixed on a whirl mixer for 20 seconds. The mixture was allowed to dwell for 10 minutes and the denaturated proteins were centrifuged at 2500 rpm. The extraction yield was 72 % of the $T_4$ initially present.

The thyroxine content was determined by pipetting each 0.3 ml of the alcoholic extract in measuring vials which contain 3.3 ml of a TBG solution prepared according to known methods of column chromatography and 0.02 $\mu$Ci/ml of thyroxine labelled with $^{125}$I. To draw the standard curve each 0.3 ml of a standard solution of 5 and 20 $\mu$g of thyroxine/100 ml were treated in the same manner. The adsorption vials were put on the measuring vials, the devices were closed and the total radioactivity of the solutions was measured after thorough mixing. To adsorb the free $T_4$-$^{125}$I-activity the devices were turned headover on a rotator at 13 rpm for 60 minutes at room temperature. The devices were set upright so that the solution flowed from the adsorption vials entirely into the measuring vials, where the residual radioactivity which had remained in the solution was measured. Then, the quotient $$G = \frac{\text{residual radioactivity}}{\text{total radioactivity}} \cdot 100$$

was calculated for each sample. The values obtained for the standard samples were inserted into a diagram against the amounts of thyroxine contained in the standard solutions and the two points were joined with a straight line, thus giving the standard curve. The unknown content of the sera to be examined would now be evaluated by means of the quotient G of the standard curve. The thyroxine content of the serum results from the value read off and the extraction yield.

The TBG solution mentioned above was prepared from a fraction containing TBG which was obtained upon purifying the serum by column chromatography (so-called "cast II" (Abguss II) according to K. Heide and H. Haupt, Behringwerke Mitteilungen vol. 43, 1964, 161). In this process the corresponding fraction is, at first, dialysed against water and then diluted with 0.1 M tris-(hydroxymethyl)-aminomethane/HCl buffer to give a total protein content of 0.022 g/100 ml. The solution was stabilized and conserved by adding 0.02 percent by weight of $NaN_3$.

What is claimed is:

1. In a process for determining the concentration of a hormone in a measured amount of liquid which comprises adding thereto measured amounts of radioactively-labelled hormone and of a hormone-binding protein or antibody, contacting the liquid mixture with an ion exchange resin for adsorbing unbound hormone, and then determining the residual radioactivity of the liquid mixture, the improvement wherein said liquid mixture is introduced into a measuring vial, the measuring vial is connected to an adsorption vial formed from a mixture of a thermoplastic resin and an ion exchange resin adsorbing said hormone, the connected measuring and adsorption vials are sealed, the liquid mixture is brought into contact with the walls of the adsorption vial for adsorption of unbound hormone, and the liquid mixture is then drained into said measuring vial for determination of residual radioactivity.

2. A process as in claim 1 wherein said measuring vial and adsorption vial are cylindrical, are connected along their cylindrical axis, and wherein said liquid mixture is contacted with the walls of said adsorption vial by rotation of the connected vials about an axis 90° to the cylindrical axis.

3. A process claimed in claim 1, wherein the concentration of hormones in the blood is determined.

4. A process claimed in claim 1, wherein the TBG capacity of the blood serum is indirectly determined, the radioactive indicator used being L-triiodothyronine labelled with $^{125}$I or $^{131}$I.

5. A process as claimed in claim 1, wherein the concentration of thyroxine in the blood is determined, the radioactive indicator used being thyroxine labelled with $^{125}$I or $^{131}$I.

6. A device for determining the hormone content of a liquid by the addition to said liquid of a radioactively-labelled hormone and a hormone-binding protein or antibody and contact of the mixture with an ion exchange resin for adsorbing unbound hormone, said device comprising a first measuring vial for containing said liquid mixture, said measuring vial having an open end, a second adsorption vial open at both ends detachably connected at one end with the open end of said measuring vial and having closure means at the other end thereof, said adsorption vial being formed from a mixture of a thermoplastic resin and an ion exchange resin adsorbing said hormone.

7. A device as in claim 6 wherein said adsorption vial is formed from a mixture of thermoplastic resin and ion exchange resin containing from 10 to 60 percent by weight of said ion exchange resin.

8. A device as in claim 6 wherein said adsorption vial is formed from a mixture of high pressure polyethylene and ion exchange resin containing from 20 to 40 percent by weight of said ion exchange resin.

9. A deive as in claim 6 wherein said ion exchange resin is admixed with said thermoplastic resin, prior to forming said adsorption vial, as particles having an average particle size from 0.04 to 1 mm in diameter, an exchanger capacity of 0.3 to 3 Val/1, and a cross-linked moiety between 1 and 12 percent.

10. A device as in claim 6 wherein said ion exchange resin is admixed with said thermoplastic resin, prior to forming said adsorption vial, as particles having an average particle size from 0.08 to 0.2 mm in diameter, an exchanger capacity of 0.5 to 1.5 Val/1, and a cross-linked moiety between 4 and 10 percent.

11. A device as in claim 6 wherein said ion exchange resin is an anion exchanger having quaternary amino groups capable of being ionized.

* * * * *